(12) United States Patent
Tanaka et al.

(10) Patent No.: US 9,051,256 B1
(45) Date of Patent: Jun. 9, 2015

(54) PROCESS FOR PRODUCING HYDROXY ADAMANTANE CARBOXYLIC ACID COMPOUNDS

(71) Applicant: Mitsubishi Gas Chemical Company, Inc., Tokyo (JP)

(72) Inventors: Hiroyasu Tanaka, Tokyo (JP); Yoshio Nishimura, Tokyo (JP); Kikuo Furukawa, Tokyo (JP); Shoichi Hayakawa, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 14/328,973

(22) Filed: Jul. 11, 2014

Related U.S. Application Data

(60) Provisional application No. 61/970,328, filed on Mar. 25, 2014.

(51) Int. Cl.
*C07C 51/367* (2006.01)
*C07C 51/31* (2006.01)

(52) U.S. Cl.
CPC .............. *C07C 51/367* (2013.01); *C07C 51/316* (2013.01); *C07C 2103/74* (2013.01)

(58) Field of Classification Search
None
See application file for complete search history.

(56) References Cited

U.S. PATENT DOCUMENTS

| 6,392,104 B1 | 5/2002 | Ishii et al. |
| RE39,744 E | 7/2007 | Ishii et al. |
| 2005/0158662 A1 | 7/2005 | Furukawa et al. |

FOREIGN PATENT DOCUMENTS

| JP | H04-39665 A | 2/1992 |
| JP | H06-305044 A | 11/1994 |
| JP | H11-106360 A | 4/1999 |
| JP | 2006-016379 A | 1/2006 |
| JP | 2007-136443 A | 6/2007 |
| JP | 2010-150220 A | 7/2010 |
| JP | 2014-009171 A | 1/2014 |

OTHER PUBLICATIONS

Zhurnal Organicheskoi Khimii, 1992, vol. 28, #10, 2098.

*Primary Examiner* — Yevegeny Valenrod
(74) *Attorney, Agent, or Firm* — Fitch, Even, Tabin & Flannery LLP

(57) ABSTRACT

The present invention can provide a process for producing a hydroxy adamantane carboxylic acid compound represented by the above formula (2), which comprises (i) reacting an adamantane compound represented by the above formula (1) with carbon monoxide or with a carbon monoxide source in a proton acid solution prepared at a concentration of 90% by mass or more to thereby cause carboxylation of the OX group(s), and then (ii) adding an oxidizing agent to the reaction mixture to cause oxidation of the bridgehead C—H bond to thereby generate a hydroxyl group.

7 Claims, No Drawings

PROCESS FOR PRODUCING HYDROXY ADAMANTANE CARBOXYLIC ACID COMPOUNDS

CROSS REFERENCE TO RELATED APPLICATION

This application is a U.S. Utility application which claims the benefit of U.S. Provisional Application No. 61/970,328, filed Mar. 25, 2014, the complete disclosure of which is incorporated herein by reference.

TECHNICAL FIELD

The present invention relates to a process for preparation of hydroxy adamantane carboxylic acid compounds which have an adamantane skeleton and are useful as intermediates for pharmaceuticals and agrochemicals, as optical materials (e.g., optical fibers, optical waveguides, optical disk substrates, photoresists), as starting materials for functional resins excellent in heat resistance, surface hardness and other properties, or as various other industrial products.

BACKGROUND ART

Alicyclic compounds having bridgeheads as appear in an adamantane skeleton are structurally rigid and have high heat resistance and excellent optical properties; and hence these compounds are used as highly functional resin materials, as intermediates for pharmaceuticals and agrochemicals, or as optical materials including photoresist materials (see, e.g., Patent Documents 1 to 3). Among them, hydroxy adamantane carboxylic acid compounds having both hydroxyl and carboxyl groups in the same molecule are advantageous in that they can be modified to have various functional groups by means of the difference in reactivity between hydroxyl and carboxyl groups, and therefore can be used as monomers for improving the performance of photoresists or as intermediates for pharmaceuticals and agrochemicals.

Several routes are known for synthesis of hydroxy adamantane carboxylic acid compounds. First, hydroxy adamantane carboxylic acid compounds are known to be generated as by-products in cases where adamantane carboxylic acid compounds are obtained from adamantanol derivatives or adamantanepolyol derivatives through the Koch reaction (see, e.g., Patent Document 4). However, there is a problem of low yield because hydroxy adamantane carboxylic acid compounds per se are not main target products and hence are difficult to isolate and purify. Moreover, there is disclosed a process for synthesis of hydroxy adamantane carboxylic acid compounds through oxygen oxidation reaction of adamantane carboxylic acid compounds, but this process has a problem in that the target compounds are difficult to isolate and purify because the reaction selectivity is low and the oxidation reaction proceeds at multiple positions to generate by-products (see, e.g., Patent Document 5). Further, there are also disclosed other processes, e.g., in which adamantane carboxylic acid compounds are halogenated and then substituted with hydroxyl groups (see Non-patent Document 1 and others), but these processes have problems in that the reaction should be conducted in two steps and thereby requires complicated and expensive operations and in that it is necessary to use halides which are high in environmental load.

PRIOR ART DOCUMENTS

Patent Documents

Patent Document 1: Japanese Patent Laid-open Publication No. H06-305044
Patent Document 2: Japanese Patent Laid-open Publication No. H04-39665
Patent Document 3: Japanese Patent Laid-open Publication No. 2006-16379
Patent Document 4: Japanese Patent Laid-open Publication No. 2010-150220
Patent Document 5: Japanese Patent Laid-open Publication No. H11-106360

Non-Patent Documents

Non-patent Document 1: Zhurnal Organicheskoi Khimii, 1992, vol. 28, #10, 2098

SUMMARY OF THE INVENTION

Problem to be Solved by the Invention

The present invention has been made in view of each problem mentioned above and aims to provide a low-cost and simple process for preparation of a hydroxy adamantane carboxylic acid compound by one-pot reaction starting from an adamantane compound without being converted into a halide form.

Means to Solve the Problem

As a result of extensive and intensive efforts, the inventors of the present invention have found that the above problems can be solved by a process in which a specific adamantane compound is subjected sequentially to a carboxylation reaction and an oxidation reaction for hydroxyl group generation, which are conducted in a one-pot fashion, to thereby prepare a hydroxy adamantane carboxylic acid compound. This finding led to the completion of the present invention.

Namely, the present invention is directed to a process for preparation of a hydroxy adamantane carboxylic acid compound represented by formula (2), which comprises (i) reacting an adamantane compound represented by formula (1) with carbon monoxide or with a carbon monoxide source in a proton acid solution prepared at a concentration of 90% by mass or more to thereby cause carboxylation of the OX group(s), and then (ii) adding an oxidizing agent to the reaction mixture to cause oxidation of the bridgehead C—H bond to thereby generate a hydroxyl group:

[Formula 1]

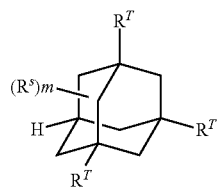

wherein the substituents $R^T$ are bridgehead substituents and represent n units of OX group, p units of hydrogen atom and q units of alkyl group containing 1 to 6 carbon atoms, where n, p and q are integers satisfying the relationship: n=1 to 3, n+p+q=3; wherein X is selected from the group consisting of a hydrogen atom, an alkyl group, an aryl group, a carbonyl group, an alkoxycarbonyl group, a tetrahydropyranyl group, a sulfonyl group and a silyl group, which may be the same or different in n units of OX group; and wherein the substituents $R^S$ are each attached to any carbon other than the bridgehead carbons, and they may be the same or different and each represent a hydrogen atom or an alkyl group containing 1 to 6 carbon atoms, where m=12;

[Formula 2]

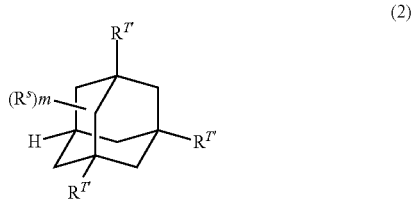

(2)

wherein the substituents $R^{T'}$ represent n units of COOH, p units of hydrogen and q units of alkyl group containing 1 to 6 carbon atoms, where n, p and q are the same as defined in formula (1).

Effects of the Invention

According to the present invention, an efficient process is provided for preparation of hydroxy adamantane carboxylic acid compounds which are useful as intermediates for pharmaceuticals and agrochemicals, as optical materials (e.g., optical fibers, optical waveguides, optical disk substrates, photoresists), as starting materials for functional resins excellent in heat resistance, surface hardness and other properties, or as various other industrial products. This process not only allows easy control of the reactions in a one-pot fashion to thereby simplify the purification process, but also has a reduced environmental load because there is no need to convert the starting compound into a halide form.

EMBODIMENTS FOR CARRYING OUT THE INVENTION

The present invention is directed to a process in which carboxylation and oxidation reactions are performed continuously on a specific adamantane compound in a one-pot fashion to prepare a hydroxy adamantane carboxylic acid compound. The embodiments of the present invention will be described in more detail below.

The adamantane compound used as a starting material in the present invention is an adamantane compound having an OX group(s), which satisfies the chemical structure represented by formula (1). Such an OX group is a monovalent organic group composed of an oxygen atom and X attached thereto (where X is a hydrogen atom, an alkyl group, an aryl group, a carbonyl group, an alkoxycarbonyl group, a tetrahydropyranyl group, a sulfonyl group or a silyl group), wherein the oxygen atom is attached to the adamantane skeleton. Among such compounds, preferred for use are those in which the OX group(s) is/are each a hydroxyl group (X is a hydrogen atom), i.e., adamantanol derivatives and adamantanepolyol derivatives such as adamantanediol and adamantanetriol derivatives. Moreover, any carbon other than the bridgehead carbons may have a hydrogen atom or an alkyl group containing 1 to 6 carbon atoms as the substituent $R^S$.

Examples of the above adamantanol derivatives include 1-adamantanol, 3-methyl-1-adamantanol, 3,5-dimethyl-1-adamantanol, 3-ethyl-1-adamantanol, 3,5-diethyl-1-adamantanol, 3-propyl-1-adamantanol, 3,5-dipropyl-1-adamantanol and so on, which may further have an alkyl group containing 1 to 6 carbon atoms as a substituent.

Likewise, examples of adamantanediol derivatives include 1,3-adamantanediol, 5-methyl-1,3-adamantanediol, 5-ethyl-1,3-adamantanediol, 5-propyl-1,3-adamantanediol and so on, which may further have an alkyl group containing 1 to 6 carbon atoms as a substituent.

Likewise, examples of adamantanetriol derivatives include 1,3,5-adamantanetriol and so on, which may further have an alkyl group containing 1 to 6 carbon atoms as a substituent.

X in the OX group(s) in the adamantane compound represented by formula (1) is selected from the group consisting of a hydrogen atom, an alkyl group, an aryl group, a carbonyl group, an alkoxycarbonyl group, a tetrahydropyranyl group, a sulfonyl group and a silyl group, which may be the same or different in n units of OX group.

A proton acid used as a solvent for (i) carboxylation reaction and (ii) oxidation reaction in the present invention is required to have a concentration of 90% by mass or more, and specific examples include inorganic acids (e.g., sulfuric acid), organic carboxylic acids (e.g., formic acid, acetic acid, propionic acid), and organic sulfonic acids (e.g., ethanesulfonic acid, propanesulfonic acid, trifluoromethylsulfonic acid, paratoluenesulfonic acid), which may be used either alone or in combination. Among them, sulfuric acid is preferred because it is available in a solution state, in terms of the selectivity in the reaction for obtaining a hydroxy adamantane carboxylic acid compound and the necessity to use the proton acid per se as a solvent. Moreover, in the case of using sulfuric acid, it is preferably used in the form of a 95% by mass or more aqueous solution. Within this range, the carboxylation reaction will proceed rapidly to give the hydroxy adamantane carboxylic acid compound in high yield. Further, to maintain the sulfuric acid concentration during the reaction, fuming sulfuric acid may be added before and/or during the reaction.

The amount of a proton acid solvent to be used is desirably set to 1- to 20-fold by mass, preferably 2- to 16-fold by mass, more preferably 4- to 12-fold by mass, relative to the adamantane compound of formula (1). Within this range, for example, the carboxylation reaction of the OX group(s) is allowed to proceed sufficiently and the operations of separation and purification can be conducted with a small amount of an organic solvent or water.

In the present invention, carbon monoxide or a carbon monoxide source is used for carboxylation. The amount of carbon monoxide or a carbon monoxide source to be used is preferably within the range of 0.9 to 10 equivalents, relative to the OX group(s) in the adamantane compound of formula (1), for efficient preparation of the desired hydroxy adamantane carboxylic acid compound.

Carbon monoxide used for this purpose may be pure carbon monoxide or may be diluted before use with an inert gas such as nitrogen, helium, argon, etc. Moreover, carbon monoxide may be used under normal pressure or under elevated pressure in an autoclave, and may also be blown into the reaction mixture during the reaction.

Examples of a carbon monoxide source include formic acid and formic acid alkyl esters whose alkyl group contains 1 to 10 carbon atoms, any two or more of which may be used in combination.

Specific examples of formic acid alkyl esters include methyl formate, ethyl formate, propyl formate, butyl formate, pentyl formate, hexyl formate, heptyl formate, octyl formate, nonyl formate, decanyl formate, cyclohexyl formate and so on.

Any two or more of these formic acid and formic acid alkyl esters may be used in combination, and may further be used in combination with carbon monoxide. Among these formic acid and formic acid alkyl esters, formic acid and methyl formate may be preferred for use because they are inexpensive and easy to handle. It should be noted that formic acid and formic acid alkyl esters are available as reagents or industrial chemicals.

In the present invention, the reaction temperature during carboxylation effected by reaction with carbon monoxide or with a carbon monoxide source in a proton acid solution may be, for example, −78° C. to 200° C., preferably −20° C. to 100° C., and more preferably around 0° C. to 50° C. Within this range, the carboxylation reaction of the OX group(s) in the adamantane compound represented by formula (1) will proceed sufficiently while minimizing side reactions. On the other hand, the reaction pressure is not limited in any way. Likewise, the material of a reactor to be used is not limited in any way, but preferred is a reactor resistant to corrosion with a proton acid, as exemplified by a glass-lined or Teflon®-coated reactor. Such a reactor may have any shape and any accessory equipment.

The reaction time of the carboxylation reaction will be affected by the reaction temperature, but is not limited in any way as long as it ensures sufficient conversion of carbon monoxide or the carbon monoxide source. The carboxylation reaction is preferably performed for 1 to 100 hours, particularly within the range of 1 to 10 hours. When the reaction is performed within this range, carboxylation is allowed to proceed sufficiently for efficient preparation.

Without the need to isolate or purify the resulting product, carboxylation is followed by the step of adding an oxidizing agent to the reaction mixture to cause oxidation. Any oxidizing agent may be used for this purpose as long as it is an oxidizing agent having oxidation ability in a proton acid solvent, and specific examples include inorganic acids such as nitric acid, perchloric acid, permanganic acid and chromic acid, or peroxides such as hydrogen peroxide. In terms of yield and easy handling, nitric acid is most preferred for use.

The amount of an oxidizing agent to be used is desirably set to 0.9 to 10.0 equivalents, preferably 1.0 to 5.0 equivalents, relative to the adamantane compound represented by formula (1). Within this range, oxidation will proceed sufficiently to give the desired hydroxy adamantane carboxylic acid compound in high yield.

The reaction temperature of the oxidation step is generally within the range of −10° C. to 100° C., preferably around 0° C. to 80° C. Within this range, the oxidation reaction will proceed sufficiently while minimizing side reactions. On the other hand, the reaction pressure is not limited in any way.

The oxidizing agent may be added in any manner, and any known technique may be selected for this purpose. Moreover, the temperature during addition is not limited in any way, but it is preferably set to a temperature as close as possible to the reaction temperature of the oxidation step, in terms of avoiding side reactions.

The reaction time of the oxidation reaction will be affected by the reaction temperature, but is not limited in any way as long as it allows the oxidation reaction to proceed sufficiently. In general, the oxidation reaction is preferably performed for 1 to 100 hours, more preferably for 1 to 20 hours. When the reaction is performed within this range, oxidation is allowed to proceed sufficiently to give the desired hydroxy adamantane carboxylic acid in high yield.

In the present invention, (i) the carboxylation of the adamantane compound and (ii) the oxidation reaction for hydroxyl group generation are conducted in a one-pot fashion, and the resulting product is separated and purified only after completion of the oxidation reaction. Separation and purification processes are not limited in any way, and any known techniques may be selected for this purpose. Purification techniques for use in such a reaction system using a proton acid, as in the case of the present invention, include those in which the reaction mixture is diluted with water or neutralized with an alkaline aqueous solution to precipitate crystals of the desired product, which are then collected by filtration and dried to obtain the desired hydroxy adamantane carboxylic acid compound.

The amount of water to be used for dilution of the reaction mixture is preferably set to 1- to 50-fold by mass, more preferably 2- to 10-fold by mass, relative to the reaction mixture. Within this range, the proton acid will be diluted enough to cause sufficient precipitation of crystals of the product and to minimize loss of the product to the aqueous solution during filtration.

Alternatively, an alkaline aqueous solution may also be used to neutralize the proton acid solution. This operation may be conducted after the reaction mixture is diluted with water, or the neutralization operation may be conducted simultaneously with dilution. Examples of an alkali in the alkaline aqueous solution to be used include sodium hydroxide, potassium hydroxide, sodium carbonate, potassium carbonate, sodium bicarbonate, ammonium hydroxide, and tetraalkylammonium hydroxides such as tetramethylammonium hydroxide. In particular, sodium hydroxide or potassium hydroxide is preferred because of being inexpensive and easy to handle. The concentration of such an alkaline aqueous solution is not limited in any way, but it is preferably 1% to 30% by mass, more preferably 10% to 20% by mass, in view of ordinary handling. Moreover, the amount of an alkali to be added is preferably set to 0.1 to 1 equivalent, relative to the number of moles of protons dissociated from the proton acid used as a solvent. If an alkali is added in excess, a neutralized salt of the desired hydroxy adamantane carboxylic acid compound is partitioned into the aqueous phase and is therefore difficult to isolate. In contrast, within the above range, the pH will be maintained in the acidic range, so that crystals of the desired hydroxy adamantane carboxylic acid compound can be precipitated without the need to adjust the pH by addition of an acidic aqueous solution.

Moreover, during alkaline neutralization, the reaction system may further comprise a reducing agent for reduction of the oxidizing agent. Such a reducing agent may be exemplified by known reducing agents including sodium sulfite, sodium thiosulfate, oxalic acid, formic acid and so on, and may be added in an amount ranging from 1 equivalent to 10 equivalents, relative to the oxidizing agent. The amount to be added is more preferably set within the range of 1 equivalent to 2 equivalents. It should be noted that the operations of neutralization and reduction may be conducted at any temperature, preferably within the range of 10° C. to 40° C. in terms of operational efficiency.

The desired hydroxy adamantane carboxylic acid compound may be collected by filtration in any manner, and any known technique may be selected for this purpose, such as spontaneous filtration by gravity, pressure filtration, suction filtration, centrifugal filtration, etc. Moreover, the shape of a filter used for filtration may be selected, if desired, depending on the process and/or equipment used.

Crude crystals of the hydroxy adamantane carboxylic acid compound separated by filtration as above may further be purified by known separation means such as washing, distillation, sublimation, extraction, crystallization, recrystallization, column chromatography and so on or by any combination of these separation means to thereby obtain the hydroxy adamantane carboxylic acid compound represented by formula (2).

The desired hydroxy adamantane carboxylic acid compound is usually dried and handled in powder form. Drying may be accomplished in any manner, and air drying, heat drying, vacuum drying or the like may be selected for this purpose. Vacuum drying is preferably selected because it allows a reduction in the drying time. Likewise, the drying temperature is not limited in any way and is preferably 0° C. to 120° C., more preferably 30° C. to 80° C., under normal to reduced pressure, although the drying temperature should be selected as appropriate for the drying pressure.

EXAMPLES

The present invention will be further described in more detail by way of the following illustrative examples, which are not intended to limit the scope of the present invention.

Example 1

A glass flask was equipped with a stirrer, a thermometer, a dropping funnel and a Dimroth condenser for use as a reaction apparatus and was charged with 1-adamantanol (purity: 99%, 30.2 g), followed by addition of 96% by mass concentrated sulfuric acid (215.2 g). After the mixture was stirred at room temperature and the starting material was confirmed to be dissolved, the flask was cooled to maintain the solution temperature within the range of 10° C. to 20° C. and formic acid (9.3 g) was added dropwise thereto over 30 minutes. After completion of the dropwise addition, the mixture was reacted at a reaction temperature of 35° C. for 3 hours. When the progress of the reaction was confirmed by GC, the conversion of 1-adamantanol was found to be 100% and 1-adamantane carboxylic acid was generated in a reaction yield of 98.9%. Subsequently, while cooling the flask again to maintain the solution temperature within the range of 10° C. to 20° C., 70% nitric acid (23.1 g) was added dropwise over 30 minutes. After completion of the dropwise addition, the mixture was reacted at a reaction temperature of 35° C. for 5 hours. When the progress of the reaction was confirmed by GC, the conversion of 1-adamantane carboxylic acid was found to be 100% and 3-hydroxy adamantane-1-carboxylic acid was generated in a reaction yield of 99.2%.

A glass flask was equipped with a stirrer and a thermometer for use as a purification apparatus and was charged with sodium hydroxide (90.2 g), sodium sulfite (35.5 g) and ion exchanged water (812 g) to prepare a mixed solution of sodium hydroxide and sodium sulfite, followed by cooling the flask. To the above mixed solution, the reaction mixture containing 3-hydroxy-1-adamantane carboxylic acid was added while maintaining the solution temperature below 40° C., and the precipitated white crystals were collected by filtration and washed with water. Further, the resulting crystals were dried under reduced pressure at 40° C. for 8 hours to obtain white crystals of 3-hydroxy adamantane-1-carboxylic acid (30.0 g, yield: 85.3%).

Example 2

The same operations as conducted in Example 1 were repeated, except that the reaction mixture temperature after dropwise addition of nitric acid was set to 50° C. In the first carboxylation reaction step, the conversion of 1-adamantanol was found to be 99.0% and 1-adamantane carboxylic acid was generated in a reaction yield of 97%. In the second oxidation reaction step, the conversion of 1-adamantane carboxylic acid was found to be 99% and white crystals of 3-hydroxy adamantane-1-carboxylic acid (28.3 g, yield: 75.2%) were obtained.

Example 3

The same operations as conducted in Example 1 were repeated, except that the reaction mixture temperature after dropwise addition of nitric acid was set to 80° C. In the first carboxylation reaction step, the conversion of 1-adamantanol was found to be 99.0% and 1-adamantane carboxylic acid was generated in a reaction yield of 97%. In the second oxidation reaction step, the conversion of 1-adamantane carboxylic acid was found to be 98.0% and white crystals of 3-hydroxy adamantane-1-carboxylic acid (9.8 g, yield: 25.2%) were obtained.

Example 4

The same reaction apparatus as shown in Example 1 was charged with 1,3-adamantanediol (purity: 99%, 30.0 g), followed by addition of 96% by mass concentrated sulfuric acid (360.1 g). After the mixture was stirred at room temperature and the starting material was confirmed to be dissolved, the flask was cooled to maintain the solution temperature within the range of 10° C. to 20° C. and formic acid (16.8 g) was added dropwise thereto over 30 minutes. After completion of the dropwise addition, the mixture was reacted at a reaction temperature of 35° C. for 3 hours. When the progress of the reaction was confirmed by GC, the conversion of 1,3-adamantanediol was found to be 100% and 1,3-adamantane dicarboxylic acid was generated in a reaction yield of 92.9%. Subsequently, while maintaining the solution temperature within the range of 35° C. to 50° C., 70% nitric acid (48.2 g) was added dropwise over 30 minutes. After completion of the dropwise addition, the mixture was reacted at a reaction temperature of 50° C. for 5 hours. When the progress of the reaction was confirmed by GC, the conversion of 1,3-adamantane dicarboxylic acid was found to be 95.0% and 5-hydroxy adamantane-1,3-dicarboxylic acid was generated in a reaction yield of 64.5%.

The same purification apparatus as shown in Example 1 was charged with sodium hydroxide (154.2 g), sodium sulfite (74.2 g) and ion exchanged water (873.8 g) to prepare a mixed solution of sodium hydroxide and sodium sulfite, followed by cooling the flask. To the above mixed solution, the reaction mixture containing 5-hydroxy-1,3-adamantane dicarboxylic acid was added while maintaining the solution temperature within the range of 10° C. to 40° C., and the precipitated crystals were collected by filtration and washed with water. The crystals were dried under reduced pressure at 40° C. for 8 hours to obtain white crystals of 5-hydroxy adamantane-1,3-dicarboxylic acid (28.0 g, yield: 65.4%).

Example 5

The same reaction apparatus as shown in Example 1 was charged with 3,5-dimethyl-1-adamantanol (purity: 99%, 30.0 g), followed by addition of 96% by mass concentrated sulfuric acid (208 g). After the mixture was stirred at room temperature and the starting material was confirmed to be dissolved, the flask was cooled to maintain the solution temperature within the range of 10° C. to 20° C. and formic acid (7.76 g) was added dropwise thereto over 30 minutes. After completion of the dropwise addition, the mixture was reacted at a reaction temperature of 35° C. for 3 hours. When the progress of the reaction was confirmed by GC, the conversion of 3,5-dimethyl-adamantanol was found to be 100% and 3,5-dimethyl-1-adamantane carboxylic acid was generated in a reaction yield of 92.6%. Subsequently, while cooling the flask again to maintain the solution temperature within the range of 10° C. to 20° C., 70% nitric acid (19.6 g) was added dropwise over 30 minutes. After completion of the dropwise addition, the mixture was reacted at a reaction temperature of 50° C. for 5 hours. When the progress of the reaction was confirmed by GC, the conversion of 3,5-dimethyl-1-adamantane carboxylic acid was found to be 100% and 3-hydroxy-5,7-dimethyladamantane-1-carboxylic acid was generated in a reaction yield of 98.0%.

The same purification apparatus as shown in Example 1 was charged with sodium hydroxide (90.2 g), sodium sulfite (35.5 g) and ion exchanged water (812 g) to prepare a mixed solution of sodium hydroxide and sodium sulfite, followed by cooling the flask. To the above mixed solution, the reaction mixture containing 3-hydroxy-5,7-dimethyladamantane-1-carboxylic acid was added while maintaining the solution temperature within the range of 10° C. to 40° C., and the precipitated crystals were collected by filtration and washed with water. The crystals were dried under reduced pressure at 40° C. for 8 hours to obtain white crystals of 3-hydroxy-5,7-dimethyladamantane-1-carboxylic acid (32.6 g, yield: 87.5%).

Comparative Example 1

A flask equipped with a stirrer, a thermometer, a dropping funnel and a Dimroth condenser was charged with 1-adamantanol (purity: 99%, 30.0 g), followed by addition of 96% by mass concentrated sulfuric acid (177.5 g). After the mixture was stirred at room temperature and the starting material was confirmed to be dissolved, the flask was cooled to maintain the solution temperature within the range of 10° C. to 20° C. and formic acid (9.3 g) was added dropwise thereto over 30 minutes. After completion of the dropwise addition, the mixture was reacted at a reaction temperature of 35° C. for 3 hours. When the progress of the reaction was confirmed by GC, the conversion of 1-adamantanol was found to be 100% and 1-adamantane carboxylic acid was generated in a reaction yield of 99.0%.

A flask equipped with a stirrer and a thermometer was charged with sodium hydroxide (74.5 g) and ion exchanged water (670.5 g), followed by cooling the flask. To the above sodium hydroxide solution, the reaction mixture containing 1-adamantane carboxylic acid was added while maintaining the solution temperature within the range of 10° C. to 40° C., and the precipitated crystals were collected by filtration and washed with water. The crystals were dried under vacuum at 40° C. for 8 hours to obtain white crystals of 1-adamantane carboxylic acid (31.6 g, yield: 89.0%).

Further, a flask equipped with a stirrer, a thermometer, a dropping funnel and a Dimroth condenser was charged with the resulting 1-adamantane carboxylic acid (31.6 g), followed by addition of 96% by mass concentrated sulfuric acid (215.2 g). After the mixture was stirred at room temperature and the starting material was confirmed to be dissolved, the flask was cooled to maintain the solution temperature within the range of 10° C. to 20° C. and 70% nitric acid (23.0 g) was added dropwise thereto over 30 minutes. After completion of the dropwise addition, the mixture was reacted at a reaction temperature of 35° C. for 5 hours. When the progress of the reaction was confirmed by GC, the conversion of 1-adamantane carboxylic acid was found to be 100% and 3-hydroxy adamantane-1-carboxylic acid was generated in a reaction yield of 99.2%.

Likewise, a flask equipped with a stirrer and a thermometer was charged with sodium hydroxide (90.2 g), sodium sulfite (35.5 g) and ion exchanged water (812 g) to prepare a mixed solution of sodium hydroxide and sodium sulfite, followed by cooling the flask. To the above mixed solution, the reaction mixture containing 3-hydroxy-1-adamantane carboxylic acid was added while maintaining the solution temperature within the range of 10° C. to 40° C., and the precipitated crystals were collected by filtration and washed with water. The crystals were dried under reduced pressure at 40° C. for 8 hours to obtain white crystals of 3-hydroxy adamantane-1-carboxylic acid (30.6 g, yield: 89.0%). The yield for two steps was found to be 79.2%, which was lower than the yield of Example 1.

Comparative Example 2

The same reaction apparatus as shown in Comparative Example 1 was charged with 1,3-adamantanediol (purity: 99%, 30.0 g), followed by addition of 96% by mass concentrated sulfuric acid (360 g). After the mixture was stirred at room temperature and the starting material was confirmed to be dissolved, the flask was cooled to maintain the solution temperature within the range of 10° C. to 20° C. and formic acid (16.8 g) was added dropwise thereto over 30 minutes. After completion of the dropwise addition, the mixture was reacted at a reaction temperature of 35° C. for 3 hours. When the progress of the reaction was confirmed by GC, the conversion of 1,3-adamantanediol was found to be 100% and 1,3-adamantane dicarboxylic acid was generated in a reaction yield of 92.5%.

The same purification apparatus as shown in Comparative Example 1 was charged with sodium hydroxide (154.2 g) and ion exchanged water (873.8 g), followed cooling the flask. To the above sodium hydroxide solution, the reaction mixture containing 1,3-adamantane dicarboxylic acid was added while maintaining the solution temperature within the range of 10° C. to 40° C., and the precipitated crystals were collected by filtration and washed with water. The crystals were dried under vacuum at 40° C. for 8 hours to obtain white crystals of 1,3-adamantane dicarboxylic acid (35.6 g, yield: 89.0%).

The same reaction apparatus as shown above was charged with the resulting 1,3-adamantane dicarboxylic acid (35.6 g), followed by addition of 96% by mass concentrated sulfuric acid (320.0 g). After the mixture was stirred at a temperature of 35° C. and the starting material was confirmed to be dissolved, 70% nitric acid (42.8 g) was added dropwise over 30 minutes while maintaining the solution temperature within the range of 35° C. to 50° C. After completion of the dropwise addition, the mixture was reacted at a reaction temperature of 50° C. for 5 hours. When the progress of the reaction was confirmed by GC, the conversion of 1,3-adamantane dicarboxylic acid was found to be 100% and 5-hydroxy adamantane-1,3-dicarboxylic acid was generated in a reaction yield of 75.0%.

The same purification apparatus as shown above was charged with sodium hydroxide (137.2 g), sodium sulfite (66.0 g) and ion exchanged water (777 g) to prepare a mixed solution of sodium hydroxide and sodium sulfite, followed by cooling the flask. To the above mixed solution, the reaction mixture containing 5-hydroxy adamantane-1,3-dicarboxylic acid was added while maintaining the solution temperature within the range of 10° C. to 40° C., and the precipitated crystals were collected by filtration and washed with water.

The crystals were dried under reduced pressure at 40° C. for 8 hours to obtain white crystals of 5-hydroxy adamantane-1,3-dicarboxylic acid (25.6 g, yield: 67.2%). The yield for two steps was found to be 60.0%, which was lower than the yield of Example 4.

Comparative Example 3

The same operations as conducted in Example 1 were repeated, except that 85% by mass sulfuric acid was used in place of concentrated sulfuric acid. In the first carboxylation reaction step, the conversion of 1-adamantanol was found to be 37.7% and 1-adamantane carboxylic acid was generated in a reaction yield of 12.9%. When compared to Example 1, the yield in the first carboxylation reaction step was reduced.

Comparative Example 4

The same operations as conducted in Example 1 were repeated, except that 85% by mass phosphoric acid was used in place of concentrated sulfuric acid. As a result, the first carboxylation reaction step did not proceed.

Comparative Example 5

The same reaction apparatus as shown in Example 1 was charged with 1-bromoadamantane (purity: 99%, 15.1 g), followed by addition of 96% by mass concentrated sulfuric acid (76.2 g). After the mixture was stirred at room temperature and the starting material was confirmed to be dissolved, the flask was cooled to maintain the solution temperature within the range of 10° C. to 20° C. and formic acid (3.4 g) was added dropwise thereto over 30 minutes. After completion of the dropwise addition, the mixture was reacted at a reaction temperature of 35° C. for 4 hours. When the progress of the reaction was confirmed by GC, the conversion of 1-bromoadamantane was found to be 89.5% and 1-adamantane carboxylic acid was generated in a reaction yield of 86.1%. Subsequently, while cooling the flask again to maintain the solution temperature within the range of 10° C. to 20° C., 70% nitric acid (8.2 g) was added dropwise over 30 minutes. After completion of the dropwise addition, the mixture was reacted at a reaction temperature of 35° C. for 3 hours. When the progress of the reaction was confirmed by GC, the conversion of 1-adamantane carboxylic acid was found to be 78.4% and 3-hydroxy adamantane-1-carboxylic acid was generated in a reaction yield of 10%.

The same purification apparatus as shown in Example 1 was charged with sodium hydroxide (48.8 g), sodium sulfite (12.6 g) and ion exchanged water (439 g) to prepare a mixed solution of sodium hydroxide and sodium sulfite, followed by cooling the flask. To the above mixed solution, the reaction mixture containing 3-hydroxy adamantane-1-carboxylic acid was added while maintaining the solution temperature within the range of 10° C. to 40° C., and the precipitated crystals were collected by filtration and washed with water. The crystals were dried under reduced pressure at 40° C. for 8 hours to obtain white crystals of 3-hydroxy adamantane-1-carboxylic acid (1.0 g, yield: 7.7%).

Tables 1 and 2 summarize the results of carboxylation reaction and oxidation reaction, respectively, obtained for each of the examples and comparative examples.

TABLE 1

| Carboxylation reaction | Adamantane compound | Reaction step | Proton acid solvent | Carbon monoxide source | Carboxylation temperature (° C.) | Conversion (%) | Reaction yield (%) |
|---|---|---|---|---|---|---|---|
| Example 1 | AD(OH) | One pot | 96% Sulfuric acid | Formic acid | 35 | 100 | 98.9 |
| Example 2 | AD(OH) | ↑ | ↑ | ↑ | ↑ | 99.0 | 97.0 |
| Example 3 | AD(OH) | ↑ | ↑ | ↑ | ↑ | 99.0 | 97.0 |
| Example 4 | AD(OH)2 | ↑ | ↑ | ↑ | ↑ | 100 | 92.9 |
| Example 5 | DMAD(OH) | ↑ | ↑ | ↑ | ↑ | 100 | 92.6 |
| Comparative Example 1 | AD(OH) | Two step | ↑ | ↑ | ↑ | 100 | 99.0 |
| Comparative Example 2 | AD(OH)2 | ↑ | ↑ | ↑ | ↑ | 100 | 92.5 |
| Comparative Example 3 | AD(OH) | One pot | 85% Sulfuric acid | ↑ | ↑ | 37.7 | 12.9 |
| Comparative Example 4 | AD(OH) | ↑ | 85% Phosphoric acid | ↑ | ↑ | 0 | 0 |
| Comparative Example 5 | ADBr | ↑ | 96% Sulfuric acid | ↑ | ↑ | 89.5 | 86.1 |

AD(OH): 1-adamantanol
AD(OH)2: 1,3-adamantanediol
DMAD(OH): 3,5-dimethyl-1-adamantanol
ADBr: 1-bromoadamantane

TABLE 2

| Oxidation reaction | Adamantane compound | Reaction step | Proton acid solvent | Oxidizing agent | Oxidation temperature (° C.) | Conversion (%) | Yield (%) |
|---|---|---|---|---|---|---|---|
| Example 1 | AD(OH) | One pot | 96% Sulfuric acid | Nitric acid | 35 | 100 | 85.3 |
| Example 2 | AD(OH) | ↑ | ↑ | ↑ | 50 | 99.0 | 75.2 |
| Example 3 | AD(OH) | ↑ | ↑ | ↑ | 80 | 98.0 | 25.2 |
| Example 4 | AD(OH)2 | ↑ | ↑ | ↑ | 50 | 95.0 | 65.4 |
| Example 5 | DMAD(OH) | ↑ | ↑ | ↑ | 35 | 100 | 87.5 |

TABLE 2-continued

| Oxidation reaction | Adamantane compound | Reaction step | Proton acid solvent | Oxidizing agent | Oxidation temperature (° C.) | Conversion (%) | Yield (%) |
|---|---|---|---|---|---|---|---|
| Comparative Example 1 | AD(OH) | Two step | ↑ | ↑ | 35 | 100 | 79.2 |
| Comparative Example 2 | AD(OH)2 | ↑ | ↑ | ↑ | 50 | 100 | 60.0 |
| Comparative Example 3 | AD(OH) | One pot | — | — | — | — | — |
| Comparative Example 4 | AD(OH) | ↑ | — | — | — | — | — |
| Comparative Example 5 | ADBr | ↑ | 96% Sulfuric acid | Nitric acid | 35 | 78.4 | 7.7 |

INDUSTRIAL APPLICABILITY

According to the present invention, hydroxy adamantane carboxylic acid compounds which are useful as intermediates for pharmaceuticals and agrochemicals, as optical materials, or as starting materials for functional resins excellent in heat resistance, surface hardness and other properties can be prepared by one-pot reaction in a simple manner in high yields and at low costs.

The invention claimed is:

1. A process for producing a hydroxy adamantane carboxylic acid compound represented by formula (2), which comprises (i) reacting an adamantane compound represented by formula (1) with carbon monoxide or with a carbon monoxide source in a proton acid solution prepared at a concentration of 90% by mass or more to thereby cause carboxylation of the OX group(s), and then (ii) adding an oxidizing agent to the reaction mixture to cause oxidation of the bridgehead C—H bond to thereby generate a hydroxyl group:

[Formula 1]

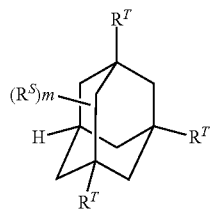

(1)

wherein the substituents $R^T$ are bridgehead substituents and represent n units of OX group, p units of hydrogen atom and q units of alkyl group containing 1 to 6 carbon atoms, where n, p and q are integers satisfying the relationship: n=1 to 3, n+p+q=3; wherein X is selected from the group consisting of a hydrogen atom, an alkyl group, an aryl group, a carbonyl group, an alkoxycarbonyl group, a tetrahydropyranyl group, a sulfonyl group and a silyl group, which may be the same or different in n units of OX group; and wherein the substituents $R^S$ are each attached to any carbon other than the bridgehead carbons, and they may be the same or different and each represent a hydrogen atom or an alkyl group containing 1 to 6 carbon atoms, where m=12;

[Formula 2]

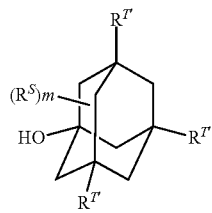

(2)

wherein the substituents $R^{T'}$ represent n units of COOH, p units of hydrogen and q units of alkyl group containing 1 to 6 carbon atoms, where n, p and q are the same as defined in formula (1).

2. The process for producing a hydroxy adamantane carboxylic acid compound according to claim 1, wherein X is a hydrogen atom.

3. The process for producing a hydroxy adamantane carboxylic acid compound according to claim 1, wherein the proton acid is sulfuric acid.

4. The process for producing a hydroxy adamantane carboxylic acid compound according to claim 1, wherein the carbon monoxide source is formic acid or a formic acid alkyl ester whose alkyl group contains 1 to 10 carbon atoms.

5. The process for producing a hydroxy adamantane carboxylic acid compound according to claim 1, wherein the reaction temperature of the carboxylation is 0° C. to 50° C.

6. The process for producing a hydroxy adamantane carboxylic acid compound according to claim 1, wherein the oxidizing agent is nitric acid.

7. The process for producing a hydroxy adamantane carboxylic acid compound according to claim 1, wherein the temperature of the oxidation reaction is 0° C. to 80° C.

* * * * *